United States Patent
Barbier et al.

(10) Patent No.: US 10,980,799 B2
(45) Date of Patent: Apr. 20, 2021

(54) CRYSTALLINE SALTS OF NALOXONE AND NALTREXONE

(71) Applicant: PAIN THERAPEUTICS, INC., Austin, TX (US)

(72) Inventors: Remi Barbier, Austin, TX (US); Nadav Friedmann, Georgetown, TX (US); Vijay Srirambhatla, Edinburgh (GB); Stephen Watt, East Lothian (GB); Michael Zamloot, Austin, TX (US)

(73) Assignee: Pain Therapeutics, Inc., Austin, TX (US)

( * ) Notice: Subject to any disclaimer, the term of this patent is extended or adjusted under 35 U.S.C. 154(b) by 48 days.

(21) Appl. No.: 15/762,237

(22) PCT Filed: Sep. 26, 2016

(86) PCT No.: PCT/US2016/053699
§ 371 (c)(1),
(2) Date: Mar. 22, 2018

(87) PCT Pub. No.: WO2017/053938
PCT Pub. Date: Mar. 30, 2017

(65) Prior Publication Data
US 2018/0263974 A1  Sep. 20, 2018

Related U.S. Application Data

(60) Provisional application No. 62/222,924, filed on Sep. 24, 2015.

(51) Int. Cl.
| | | |
|---|---|---|
| *A61K 31/485* | (2006.01) |
| *A61K 9/70* | (2006.01) |
| *C07D 489/08* | (2006.01) |
| *C07C 59/285* | (2006.01) |
| *C07C 55/10* | (2006.01) |
| *A61K 31/4468* | (2006.01) |

(52) U.S. Cl.
CPC .......... *A61K 31/485* (2013.01); *A61K 9/7038* (2013.01); *A61K 31/4468* (2013.01); *C07C 55/10* (2013.01); *C07C 59/285* (2013.01); *C07D 489/08* (2013.01)

(58) Field of Classification Search
CPC .. A61K 31/4468; A61K 9/7038; C07C 55/10; C07C 59/285; C07D 489/08
See application file for complete search history.

(56) References Cited

U.S. PATENT DOCUMENTS

| | | |
|---|---|---|
| 2005/0181041 A1 | 8/2005 | Goldman |
| 2008/0233178 A1 | 9/2008 | Reidenberg et al. |
| 2016/0081946 A1 | 3/2016 | Barbier et al. |

FOREIGN PATENT DOCUMENTS

| | | |
|---|---|---|
| CA | 2748620 | 3/2014 |
| WO | 2004/017941 A2 | 3/2004 |

OTHER PUBLICATIONS

International Search Report and Written Opinion in International Application No. PCT/US2016/053699, dated Dec. 27, 2016.

*Primary Examiner* — Genevieve S Alley
(74) *Attorney, Agent, or Firm* — J.A. Lindeman & Co. PLLC

(57) ABSTRACT

This invention relates to crystalline salts of naloxone and of naltrexone and their use as opioid antagonists. The crystalline salts of the invention include naloxone saccharinate, naltrexone succinate and a methanol solvate of naltrexone succinate. A drug-in-adhesive transdermal patch containing the opioid analgesic fentanyl or an analog thereof and a crystalline salts of naloxone or naltrexone is disclosed. Also disclosed is a method of treating pain, such as acute, chronic or intermittent pain, by applying a drug-in-adhesive transdermal patch of the invention to the skin of a patient in need thereof.

20 Claims, 5 Drawing Sheets

PLOT SHOWING THE LABELS AND THE DISORDER IN THE NALOXONE SACCHARINATE FROM THE SINGLE CRYSTAL STRUCTURE

STACK OF XRPD PATTERNS OF THE XRPD OBTAINED OF NALOXONE SACCHARINATE FROM EXAMPLE 1.1 (TOP), THE SIMULATED POWDER PATTERN FROM THE SINGLE CRYSTAL STRUCTURE AT 120K (MIDDLE) AND THE NALOXONE (BOTTOM)

TG/DTA OF NALOXONE SACCHARINATE

XRPD OF THE METHANOL SOLVATE OF NALTREXONE SUCCINATE

PLOT SHOWING THE NALTREXONE MOLECULE AND ITS LABELS IN THE METHANOL SOLVATE OF NALTREXONE SUCCINATE FROM THE SINGLE CRYSTAL STRUCTURE. METHANOL NOT SHOWN.

STACK OF XRPD PATTERNS OF THE XRPD OBTAINED FROM THE METHANOL SOLVATE OF NALTREXONE SUCCINATE (TOP), THE SIMULATED POWDER PATTERN FROM THE SINGLE CRYSTAL STRUCTURE AT 120K (MIDDLE) AND THE NALTREXONE (BOTTOM)

TG/DTA TRACES FOR NALTREXONE SUCCINATE

XRPD PATTERN OF NALTREXONE SUCCINATE FROM 1,4-DIOXANE

CRYSTALLINE SALTS OF NALOXONE AND NALTREXONE

CROSS REFERENCE TO RELATED APPLICATIONS

This application claims priority to U.S. application No. 62/222,924, filed Sep. 24, 2015, which is incorporated herein by reference.

FIELD OF THE INVENTION

This invention relates to crystalline salts of naloxone and naltrexone and their use as opioid antagonists. The invention also relates to a transdermal patch, such as a drug-in-adhesive transdermal patch, containing an analgesic such as fentanyl, which is a mu opioid agonist, or an analog of fentanyl or another mu opioid agonist; and a crystalline salt of naloxone or of naltrexone. The invention also relates to methods for treating pain.

BACKGROUND OF THE INVENTION

Fentanyl is a synthetic opioid analgesic used to treat moderate to severe chronic pain. Fentanyl, whose chemical name is chemical name is N-Phenyl-N-(1-(2-phenylethyl)-4-piperidinyl) propanamide, has the following chemical formula:

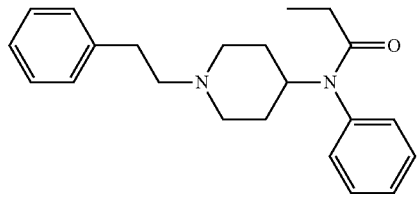 [SMILES: CCC(=O)N(c1ccccc1)C1CCN(CCc2ccccc2)CC1]

Fentanyl and its congeners, sufentanil, alfenanil and remifentanil, all act as opioid agonists mainly on mu-receptors that are present along the central nervous system. Mu-binding sites are present in the human brain, spinal cord, and other tissues that are integral to the transmission of pain pathways. Therapeutic use of intravenous fentanyl results in a rapid onset but a short duration of action, making this route of administration a popular choice as an anesthetic adjuvant. Fentanyl's low molecular weight, high potency and lipid solubility also makes it suitable for transdermal delivery. The development of transdermal fentanyl, a less invasive route of administration compared to intravenous delivery, has facilitated the use of fentanyl to manage chronic pain. Transdermal fentanyl patches such as the DURAGESIC® fentanyl transdermal system sold by Janssen Pharmaceuticals, adhere to skin and provide a prolonged, continuous, slow and therapeutic dose of fentanyl for up to 72 hours.

As with all potent mu opioid analgesics, fentanyl is also abused for its intense euphoric effects. Abusers seek rapid drug absorption. To get high, abusers often cut a small piece of the fentanyl patch and swallow it or suck on it. These actions provide abusers with a rapidly absorbed, high blood level of of fentanyl, resulting in euphoric effects. Non-medicinal use of transdermal fentanyl patches is extremely dangerous and can result opioid addiction, overdose or death. Even after a 72 hour usage interval some residual fentanyl remains in the transdermal patch. Unused or used fentanyl patches are therefore also susceptible to unintentional misuse, such as accidental exposure to a transdermal fentanyl patch by children or family pets.

Methods or paradigms of abusing fentanyl transdermal patches include, for example, single or multistep extraction, physical tampering with subsequent extraction and direct administration by oral routes such as swallowing or inhaling (e.g. smoking) as well as sublingual or buccal administration, chewing and administration as a suppository. Documented methods of abusing fentanyl patches include injecting fentanyl extracted from a patch intravenously, chewing or swallowing patches, inserting patches into the rectum, inhaling fentanyl gel, and extracting fentanyl in tea. The biological effects of fentanyl are similar to those of street heroin but hundreds of times more potent. It is extremely difficult to stop its absorption because fentanyl is highly lipophilic and penetrates the central nervous system easily. Therefore, the illicit use of fentanyl is very dangerous and causes numerous opioid overdose deaths. See, W. Guan, et al., Prim Care Companion CNS Disord. 2011, 13(5) (citations omitted).

Curtailing the misuse and abuse of fentanyl and other opioid analgesics is a difficult problem. Several approaches have been tried: formulation technologies aimed at introduction of functional characteristics that deter or resist physical and chemical practices that facilitate the non-medical use of the narcotics by various routes of administration. Such formulation technologies may impart one or more of the following abuse-deterrent characteristics to the narcotic drug product: tamper resistant secondary packaging; fabrication with crush or tear resistance laminate component seven, extraction resistance, formulation with prodrugs of the narcotic active ingredient, agonist and antagonist combinations, and even nasal gels. For a discussion of these approaches, see U.S. Pat. No. 8,338,444 B1. While the prodrug approach modifies the drug itself, the other approaches look, at least to some extent, to formulation techniques.

Formulating or placing an opioid antagonist within the opioid agonist product is the basis of the agonist/antagonist approach to curtail misuse and abuse. If the opioid agonist product is misused or there is an attempt to extract the opioid agonist from the product, the opioid antagonist is released to decrease or even block the pharmacologic effect of the opioid agonist. U.S. Pat. Nos. 8,440,220 B2 and 8,747,889 B2 disclose an analgesic system for transdermal delivery of fentanyl and analogs thereof for analgesic purposes, to a subject through intact skin over an extended period of time. The disclosure of U.S. Pat. Nos. 8,440,220 B2 and 8,747,889 B2 are incorporated herein by reference. The transdermal analgesic system is reported to have reduced potential for abuse and a substantially minimized/negligible skin sensitization response from antagonist exposure. The transdermal analgesic system is intended to provide for the controlled release of the antagonist at a rate sufficient to provide an abuse limiting release rate ratio of the antagonist to the analgesic when the dosage form is subject to abuse. In this regard, the transdermal analgesic system is intended to provide release of the antagonist at a rate sufficient to block the opioid effects of the analgesic during abuse situations. The analgesic and antagonist layers are contained in distinct reservoir layers separated by an impermeable barrier layer. The transdermal analgesic system disclosed in U.S. Pat. Nos. 8,440,220 B2 and 8,747,889 B2, however, is not a preferred solution to potential abuse employing an antagonist reservoir and an antagonist release controlling means to modulate the ingress of water/solvent to the antagonist reservoir, to modulate the release of the antagonist during abuse while permitting the release of an antagonist at a rate to limit abuse. The transdermal analgesic system is thus complex in its formulation and in its manufacture.

In view of the existing and potential abuse and misuse of fentanyl transdermal patches there remains a need in the art to develop a fentanyl transdermal patch system which mitigates, neutralizes or prevents the effects of fentanyl when a transdermal patch is intentionally abused or accidentally misused. This invention answers that need using a novel opioid analgesic/antagonist combination.

SUMMARY OF THE INVENTION

In one embodiment this invention relates to crystalline salts of naloxone and of naltrexone and their use as opioid antagonists. The crystalline salts of the invention include saccharinatesuccinatenaloxone saccharinate, naltrexone succinate, and a methanol solvate of naltrexone succinate.

In another embodiment the invention also relates to a drug-in-adhesive transdermal patch containing the opioid analgesic fentanyl or an analog thereof and a crystalline salt of naloxone or naltrexone.

In another embodiment the invention also relates to a drug-in-adhesive transdermal patch containing a mu opioid agonist, such as fentanyl—disclosed here as a particular example, and a crystalline salts of naloxone or naltrexone, as an opioid antagonist.

Another embodiment of the invention relates to a method of treating pain, such as acute, chronic or intermittent pain, by applying a drug-in-adhesive transdermal patch according to the invention to the skin of a patient in need thereof.

BRIEF DESCRIPTION OF THE FIGS

DETAILED DESCRIPTION

Figure 1:
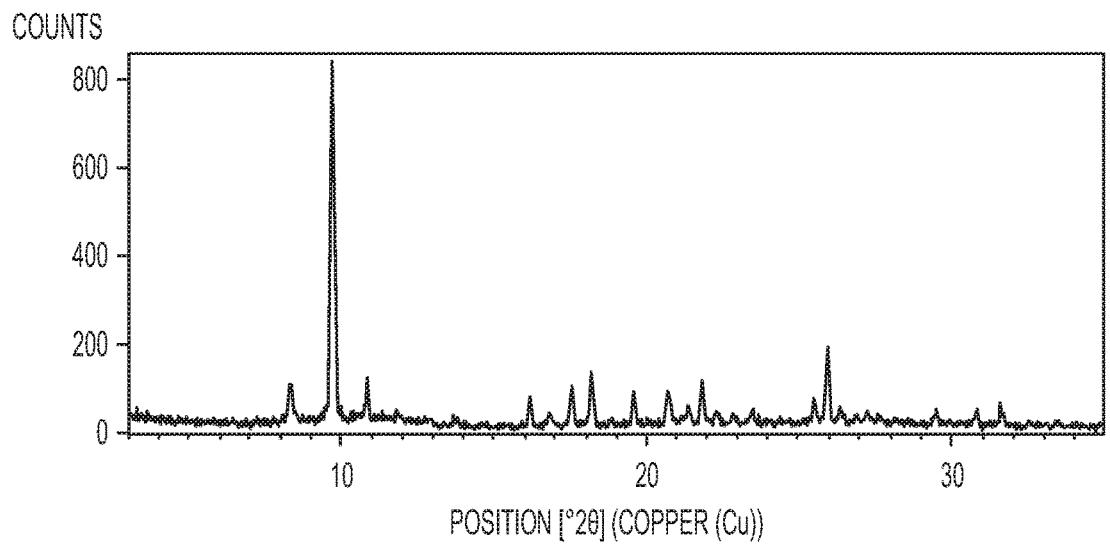
FIG. 1 depicts the experimental XRPD pattern of the naloxone saccharinate prepared in Example 1.1.

Naloxone, 17-allyl-4,5α-epoxy-3,14-dihydroxymorphinan-6-one, is an opioid receptor antagonist, having the following chemical structure:

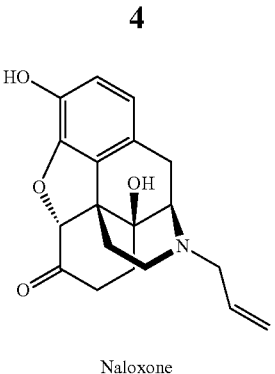

Naloxone

Naltrexone, 17-(cyclopropylmethyl)-4,5α-epoxy-3,14-dihydroxymorphinan-6-one, is an opioid receptor antagonist, having the chemical structure shown below.

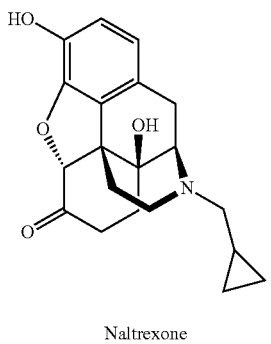

Naltrexone

Pharmaceutical uses of naltrexone as an active pharmaceutical ingredient (API) include management of alcohol dependence, opioid overdose and opioid dependence. Pharmaceutical uses of naloxone as an active pharmaceutical ingredient (API) include opioid overdose and opioid dependence. U.S. Pat. Nos. 8,440,220 B2 and and 8,747,889 B2 disclose naltrexone and naloxone as an opioid antagonist used in their transdermal system.

In one embodiment this invention relates to crystalline salts of naloxone and of naltrexone and their use as an opioid antagonist. It is well-known that crystalline materials obtain their fundamental physical properties from the molecular arrangement within the solid, and altering the placement and/or interactions between these molecules can, and usually does, have a direct impact on the properties of the particular solid. See, Schultheiss and Newman, "Pharmaceutical Cocrystals and Their Physiochemical Properties", Crystal Growth & Design, Vol. 9, No. 6, 2950-2967 (2009). Recently, crystalline forms of API's have been used to alter the physicochemical properties of a particular API. Each crystalline form of a drug candidate can have different solid state (physical and chemical) properties. The differences in physical properties exhibited by a novel solid form of an API (such as a crystalline salt, cocrystal or polymorph of the original therapeutic compound) affect pharmaceutical parameters such as storage stability, compressibility and density (important in formulation and product manufacturing), and solubility and dissolution rates, permeability, hydrophilic or lipophilic character (important factors in determining drug delivery). Because these practical physical properties are influenced by the solid state properties of the crystalline form of the API, they can provide advantages for the pharmaceutical utility and formulation of the API.

Obtaining crystalline forms of an API is extremely useful in pharmaceutical development as it may affect the in vivo disposition of the active moiety, affect the rate or extent of its release from the dosage form or even enable its suitability for a particular dosage form design. It also may permit better characterization of the API's chemical and physical properties. It is also possible to achieve desired properties of a particular API by forming a crystalline salt of the API. Crystalline forms often have better chemical and physical properties than the free base in its amorphous state. Another potentially important solid state property of an API is its dissolution rate in aqueous fluids or in polymeric preparations used to formulate the API. Such crystalline forms may, as with the crystalline salts of the invention, possess more favourable pharmaceutical and formulation properties or be easier to process than known forms of the API itself.

This invention relates to crystalline salts of naloxone and of naltrexone, as described in the examples below. The crystalline salts of the invention are naloxone saccharinate, naltrexone succinate and a methanol solvate of naltrexone succinate. A crystalline salt of an API, such as naloxone or naltrexone, is a distinct chemical composition of the API and a salt former(s) and generally possesses distinct crystallographic and spectroscopic properties when compared to those of naloxone, naltrexone and a particular salt former individually. Crystallographic and spectroscopic properties of crystalline forms are typically measured by X-ray powder diffraction (XRPD), single crystal X-ray crystallography, and infra-red spectroscopy, among other techniques. Crystalline forms often also exhibit distinct thermal behavior. Thermal behavior is measured in the laboratory by such techniques as capillary melting point, thermogravimetric analysis (TGA) and differential scanning calorimetry (DSC). The crystalline salts of the invention and the methods used to characterize them are described in the examples below.

Figure 2:
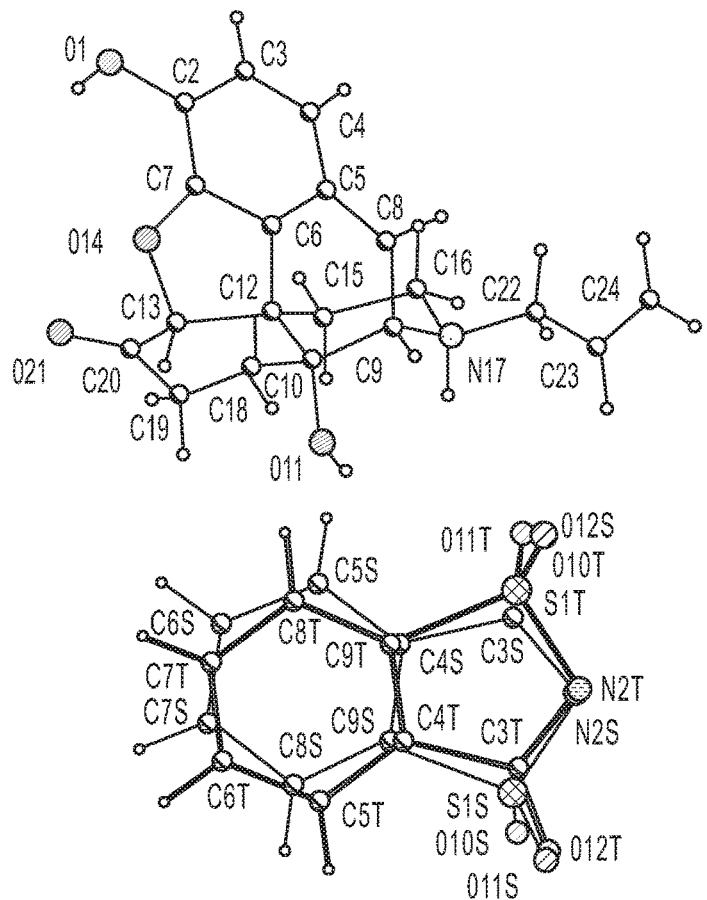
FIG. 2 is a plot showing the labels and the disorder in the naloxone saccharinate from the single crystal structure prepared in Example 1.1.
Figure 4:
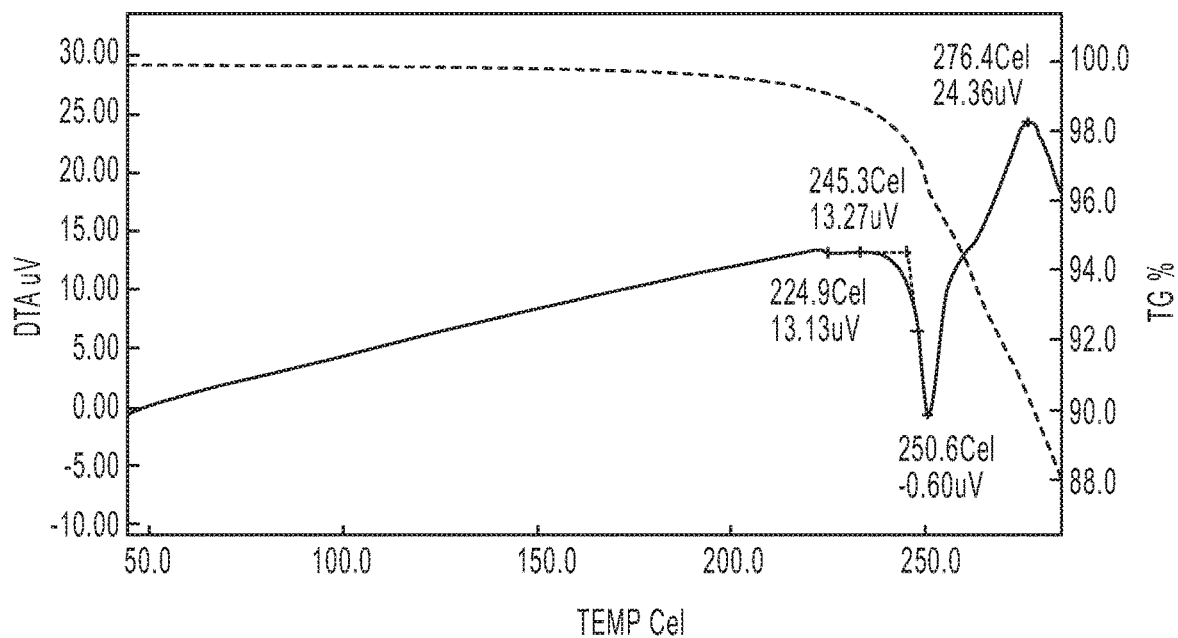
FIG. 4 depicts the TG/DTA traces for the naloxone saccharinate prepared in Example 1.1.
Figure 5:
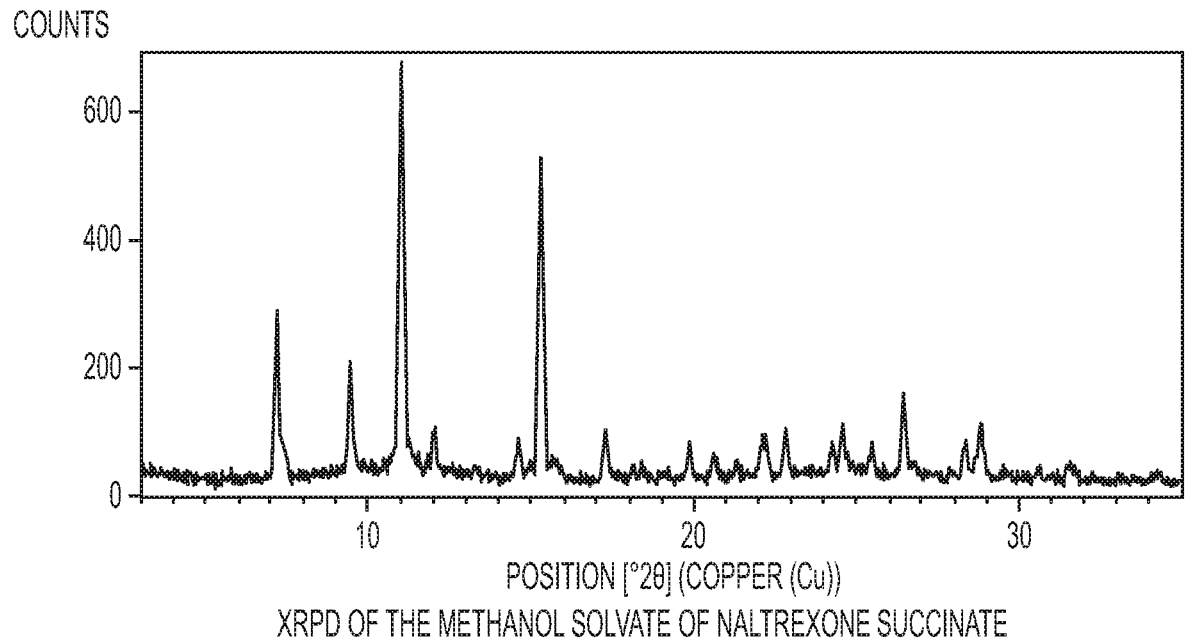
FIG. 5 depicts the experimental XRPD pattern of the methanol solvate of naltrexone succinate prepared in Example 2.1.
Figure 6:
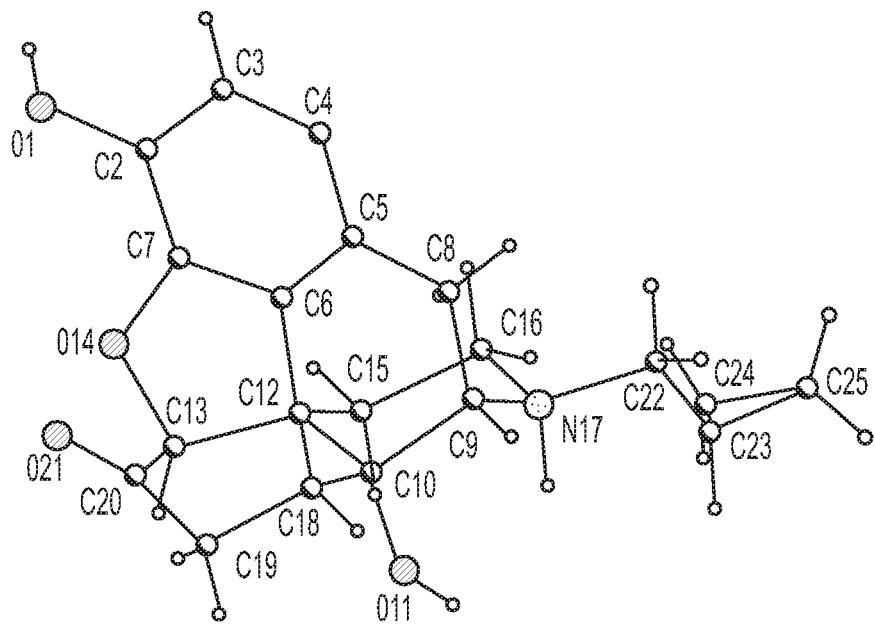
FIG. 6 is a plot showing the naltrexone molecule and its labels in the methanol solvate of naltrexone succinate from the single crystal structure prepared in Example 2.1. Methanol not shown.
Figure 8:
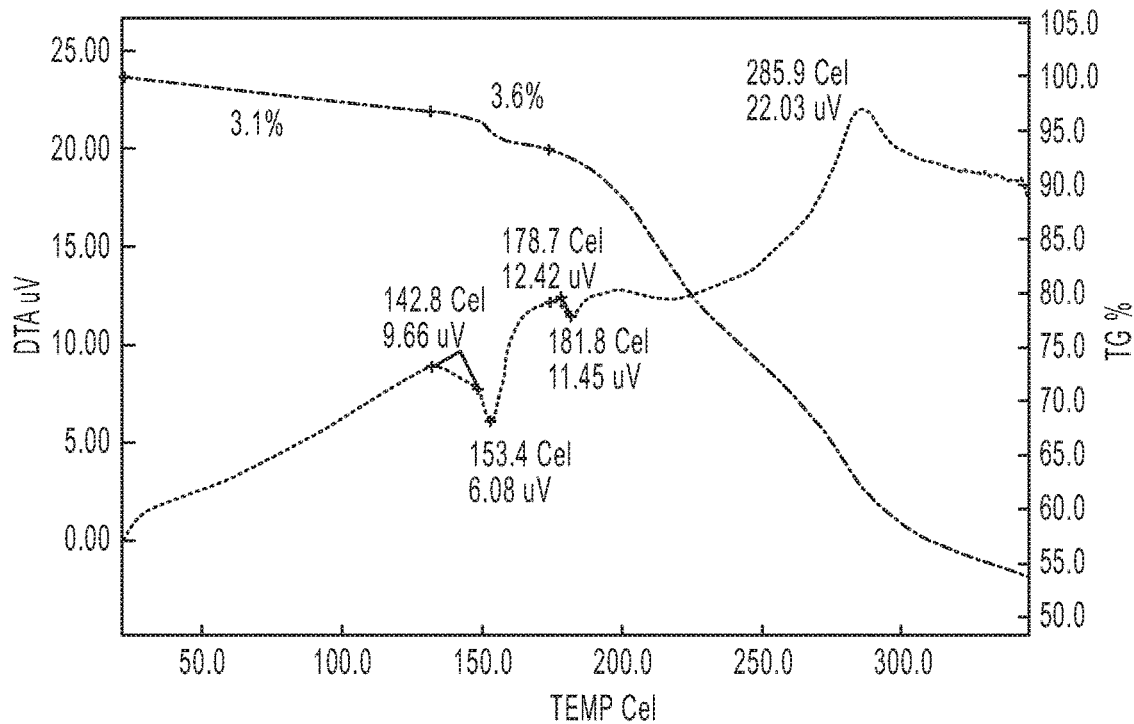
FIG. 8 depicts the TG/DTA traces for the methanol solvate of naltrexone succinate prepared in Example 2.1.
Figure 9:
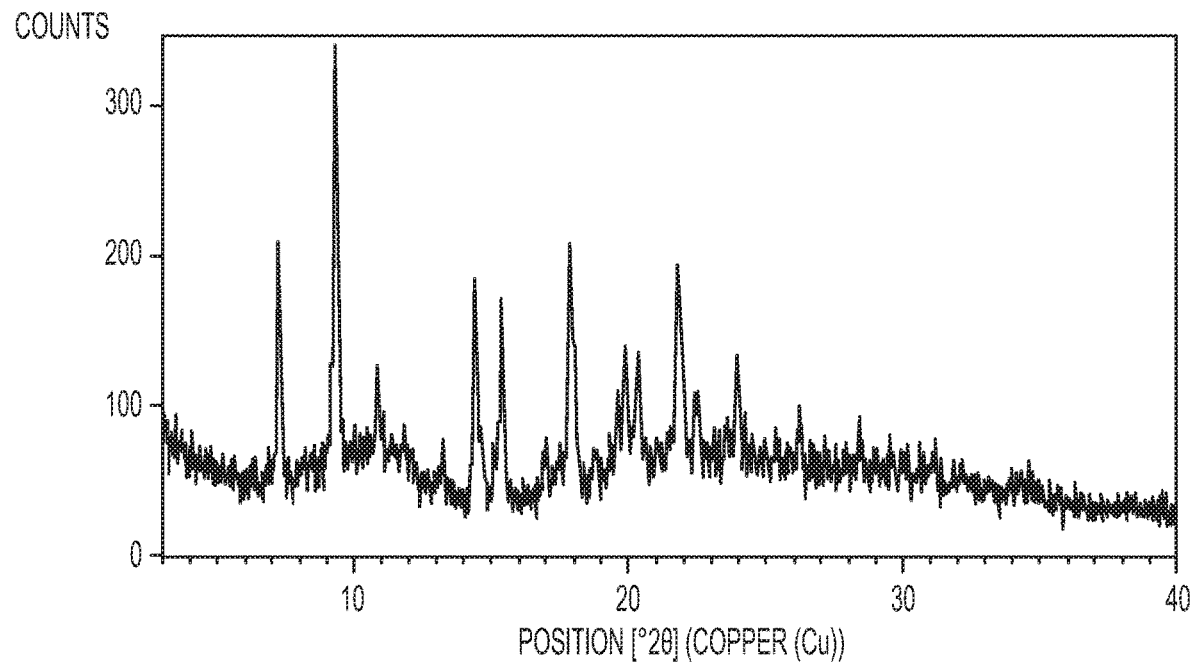
FIG. 9 depicts the experimental XRPD pattern of the naltrexone succinate from 1,4-dioxane prepared in Example 2.4.

As separate embodiments, the crystalline salts of the invention include crystalline salts of naloxone and of naltrexone selected from:

naloxone saccharinate characterized by an XRPD pattern as shown in FIG. 1, a single crystal structure as shown in FIG. 2, or a TG/DTA trace as shown in FIG. 4;

a methanol solvate of naltrexone succinate characterized by an XRPD pattern as shown in FIG. 5, a single crystal structure as shown in FIG. 6 where the methanol is not shown, or a TG/DTA trace as shown in FIG. 8; and a naltrexone succinate characterized by an XRPD pattern as shown in FIG. 9.

In another embodiment, the invention relates to a transdermal patch such as a drug-in-adhesive transdermal patch (also known as a monolithic transdermal patch) containing the analgesic such as fentanyl, which is a mu opioid agonist, or an analog of fentanyl or another mu opioid agonist and crystalline salts of naloxone and of naltrexone, as an opioid antagonist. This provides a tamper- or abuse-resistant transdermal fentanyl patch. The opioid agonist analgesic may be fentanyl or an analog thereof such as, but not limited to, alfentanil, lofentanil, remifentanil, sufentanil and trefentanil. Fentanyl is a preferred opioid analgesic. Another embodiment of the invention relates to a drug-in-adhesive transdermal patch containing a mu opioid agonist and a crystalline salt of naloxone and of naltrexone of the invention as an opioid antagonist. Combinations of crystalline salts of naloxone and of naltrexone may also be used as the opioid antagonist.

A drug-in-adhesive transdermal patch contains the drug to be delivered in an adhesive polymer matrix. The adhesive polymer matrix contains the drug, and a pressure sensitive adhesive (PSA) comprised of one or more polymers suitable for adhesion to the skin. The adhesive polymer matrix and its method of preparation should be selected such that it is compatible with fentanyl or the fentanyl analog used and such that the crystalline form of the crystalline salt of naloxone and of naltrexone used is maintained. Examples of pressure sensitive adhesives include, but are not limited to, silicones/polysiloxanes polyisobutylene (PIB), polyisoprene, polybutadiene, styrenic block polymers, and the like. Examples of styrenic block copolymer-based adhesives include, but are not limited to, styrene-isoprene-styrene block copolymer (SIS), styrene-butadiene-styrene copolymer (SBS), styrene-ethylene/butylene-styrene copolymers (SEBS), and di-block analogs thereof. These adhesive polymers are soluble in low polarity solvents and the matrix of the transdermal patch may be prepared by mixing the drug and crystalline salt into the polymer solution followed by solvent casting of the matrix layer. Alternatively, a melt blending process in which the polymer is heated to achieve a sufficiently low viscosity to allow dry mixing of the drug and crystalline salt may be employed. If the adhesive polymer matrix is formed by the melt blending and extrusion process, then polyacrylates and ethylene/vinyl acetate copolymers may be used in the adhesive polymer matrix in addition to the rubber-based adhesive polymers. Silicones are a preferred type of PSA polymers used in a drug-in-adhesive transdermal patch of the invention. Amine-compatible silicones PSA's, such as Dow Corning BioPSA 7-4101, are compatible with fentanyl free base and may be used in fentanyl-containing adhesive layers for that reason. Silicone PSAs have a low saturation solubility for fentanyl and its analogs. This allows for a zero order delivery rate of fentanyl while undissolved drug is present and after 72 hours less fentanyl remains in the patch, most having been delivered to the patient.

To prepare a drug-in-adhesive transdermal patch, the drug to be delivered, for example fentanyl or a fentanyl derivative, may first be dispersed in an oil and then the dispersion mixed into the adhesive polymer as is known the art. See, for example, U.S. Pat. No. 4,559,222, which is incorporated herein by reference. The crystalline salt of naloxone and of naltrexone used may also be dispersed as particles in the oil as long as the crystalline salt is not soluble or only sparingly soluble in the oil. Depending on the drug to be delivered and the adhesive polymer to be used, mineral oil or a silicone oil are common choices when considering PSA compatibility. The dispersion is mixed into the adhesive polymer using known blending techniques and at a shear rate is not so high as to break up the adhesive polymer. As mentioned, silicone PSA's are a preferred type of adhesive for a drug-in-adhesive transdermal patch of the invention. An example of a silicone oil is Dow-Corning 360 Medical Fluid, a linear polydimethylsiloxane (PDMS) which is available in several different viscosities. Dow-Corning 360 Medical Fluid having a viscosity of 100 cSt is a preferred silicone oil.

Figure 10:
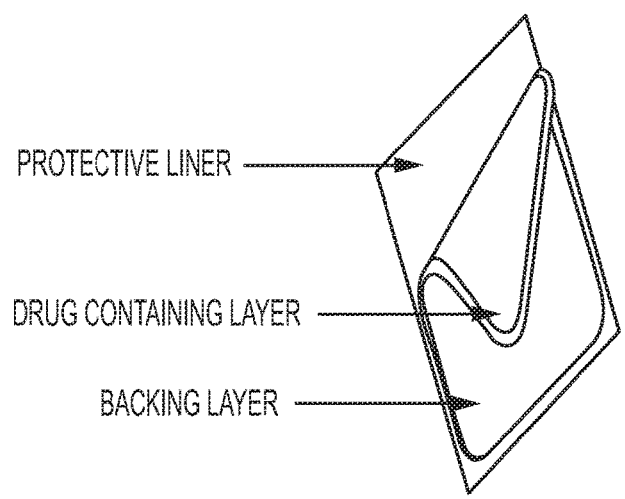
FIG. 10 depicts a drug-in-adhesive transdermal patch.

An example of a drug-in-adhesive transdermal patch used to deliver fentanyl is the DURAGESIC® fentanyl transdermal system sold by Janssen Pharmaceuticals. In the DURAGESIC® transdermal system the amount of fentanyl released from each system per hour is proportional to the surface area (25 mcg/h per 10.5 $cm^2$). The composition per unit area of all system sizes is identical. The DURAGESIC® transdermal system, shown in FIG. 10, is a rectangular transparent unit comprising a protective liner and two functional layers. Proceeding from the outer surface toward the surface adhering to skin, these layers are: a backing layer [1] composed of polyester/ethyl vinyl acetate film; and a drugin-adhesive layer [2]. Before use, a protective liner (release sheet) [3] covering the adhesive layer is removed and discarded. See, DURAGESIC® US prescribing information. Other drug-in-adhesive transdermal patch structures and variations are known in the art.

In a drug-in-adhesive transdermal patch of the invention, particles of a crystalline salt of naloxone or of naltrexone are present in the drug-in-adhesive layer as a dispersion of solid particles along with the fentanyl or an analog thereof. In an embodiment of the invention, the drug-in-adhesive layer is a monolithic layer. As known in the art, fentanyl itself is solubulized in the adhesive polymer(s) making up the drug-in-adhesive layer or present as a molecular dispersion. The crystalline salt of naloxone or of naltrexone is substantially or completely insoluble in the adhesive polymer(s), a solubility for the crystalline salt of naloxone or of naltrexone of about 0 wt % to about 1 wt % of the total adhesive polymer composition. The relative solubility of the fentanyl and insolubility of the crystalline salt of naloxone or of naltrexone provide a rate control mechanism allowing the fentanyl to be delivered to the skin and the crystalline salt of naloxone or naltrexone to be retained in the drug-in-adhesive layer. The particles of a crystalline salt of naloxone or of naltrexone are typically distributed as a dispersed powder throughout the drug-in-adhesive layer to provide a uniform composition per unit area.

A crystalline salt of naloxone or of naltrexone may be soluble in water, aqueous media certain organic solvents and mixed aqueous-organic systems; however, its insolubility in the drug-in-adhesive layer does not permit its release in any substantial or therapeutic amount in response to the moisture which may be present at the skin surface during use of the transdermal patch. The drug-in-adhesive transdermal patch of the invention, however, does release naloxone or naltrexone that dissociates from the coformer or anion present in the crystalline salt at a rate and in an amount sufficient to provide an abuse limiting dose of the opioid antagonist to the opioid analgesic when subjected to non-medical use or accidental misuse. Thus, a drug-in-adhesive transdermal patch of the invention releases naltrexone which is the dissociation product of crystalline salt of naloxone or of naltrexone as a result of the exposure to elevated temperature (i.e., a smoking paradigm of abuse) or an aqueous environment, (e.g. water or other aqueous extraction solution or saliva depending on the paradigm of abuse), and provides sufficient naltrexone to decrease or block the pharmacologic effects of the opioid during abuse or misuse situations. A transdermal patch of the invention is therapeutically equivalent to a fentanyl-only patch when the patch is administered according to prescriptive practice for a legitimate medical purpose. When the patch is misused, abused or administered inconsistently with prescribed practice, e.g., swallowed, extracted, chewed, sucked on, smoked, etc., a transdermal patch of the invention will deliver partially or fully antagonizing dose of naltrexone which imparts safety from fentanyl or opioid analgesic over-dose, which can result in death, and will reduce the rewarding effect, i.e., a "drug-liking" or euphoric effect, that is craved by drug abusers. In this way, a transdermal patch of the invention provides sufficient release of naltrexone to reduce or eliminate "drug-liking" or euphoric effects of the abuse and offers a margin of safety resulting from full or partial antagonism of fentanyl. Advantageously, a transdermal patch of the invention provides a margin of safety against abuse but also against overdose and even death.

The drug-in-adhesive layer may contain about 0.05 to about 1.75 mg/cm² of fentanyl or an analog thereof; preferably about 0.07 to about 1.50 mg/cm² of fentanyl or an analog thereof; about 0.08 to about 1.25 mg/cm² of fentanyl or an analog thereof; about 0.09 to about 1.0 mg/cm² of fentanyl or an analog thereof; about 0.1 to about 0.75 mg/cm² of fentanyl or an analog thereof; or about 0.12 to about 0.5 mg/cm² of fentanyl or an analog thereof. For other mu opioid agonists the drug-in-adhesive layer may contain the same or similar amounts appropriate for the particular agonist as known in the art. The amount of crystalline salt of naloxone or of naltrexone present in the drug-in-adhesive layer is an amount sufficient to at least reduce the "drug liking" impact of the drug abuse and/or to provide a partial or full blockade of the analgesic effect. The amount of crystalline salt of naloxone or of naltrexone present in terms of the molar ratio of naltrexone to fentanyl or an analog thereof, or other mu opioid agonist used, may range from about 0.075:1 to about 30:1, about 0.25:1 to about 20:1, about 0.5:1 to about 16:1, about 0.5:1 to about 14:1, about 0.75:1 to about 12:1, about 1:1 to about 10:1, about 1.5:1 to about 8:1, about 2:1 to about 6:1, and about 2:1 to about 4:1.

As discussed above, the adhesive used in the drug-in-adhesive layer may be a standard pressure sensitive adhesives known in the art or mixtures thereof. The adhesive polymer matrix and its method of preparation should be selected such that it is compatible with fentanyl or the fentanyl analog used and such that the crystalline form of the crystalline salt of naloxone or of naltrexone used is maintained. The adhesive polymer matrix is formulated to control the release of the drug from the patch and its permeation through the skin. As known in the art, the adhesive polymer matrix may also contain plasticizers or tackifiers that modify the rheology and adhesion characteristics of the adhesive, and may additionally include a chemical permeation enhancer such as alcohols, fatty acids and esters to modify the rate of drug penetration through the skin. The drug-in-adhesive layer may optionally contain additional components such as, additives, stabilizers, dyes, diluents, pigments, carriers, inert fillers, antioxidants, excipients, gelling agents, anti-irritants, vasoconstrictors and other materials as are generally known to the transdermal art.

A drug-in-adhesive transdermal patch of the invention may be manufactured using methods known in the art. The crystalline salt of naloxone or of naltrexone particles may be incorporated into the drug-in-adhesive layer also using known methods such as melt blending. The crystalline salt of naloxone or of naltrexone particles may be dispersed in a liquid in which the crystalline salt is not soluble or only sparingly soluble (a "non-solvent") and then added to a solution of the other drug-in-adhesive layer components in that same liquid. Alternatively, the crystalline salt of naloxone or of naltrexone particles may be dispersed into the solution of the drug-in-adhesive components itself. Use of a non-solvent ensures that the crystalline salt retains its crystalline form while forming the drug-in-adhesive layer. For a crystalline salt of naloxone or of naltrexone such a liquid will generally be a non-polar organic solvent, such as, for example, heptane and the like. Alternatively, the crystalline salt of naloxone or of naltrexone particles may be incorporated into the drug-in-adhesive layer also using known methods such as melt blending.

The invention further relates to a method of treating pain, such as acute, chronic or intermittent pain, by applying a drug-in-adhesive transdermal patch according to the invention to the skin of a patient in need thereof. Accordingly the invention relates to the use of a drug-in-adhesive transdermal patch to treat pain in a patient in need thereof. Patients should apply a transdermal patch of the invention to intact, non-irritated, and non-irradiated skin on a flat surface such as the chest, back, flank, or upper arm. A transdermal patch of the invention is typically worn for up to 72 hours.

As discussed above, transdermal patches are used in the art to administer fentanyl or an analog thereof to treat pain as well as to administer other mu opioid agonists. Transdermal patches, generally speaking, are either a drug-in-adhesive style (discussed above) or a reservoir style. In a reservoir style transdermal patch, the drug to be delivered is contained in a reservoir portion with a membrane between placed between the drug reservoir and the skin. The membrane controls the release rate of drug to the skin. As known in the art, a reservoir-style transdermal patch typically has a backing layer, a drug reservoir portion, a membrane, an adhesive and a release sheet, which is removed from the patch to expose the adhesive when applying the patch to the skin. The transdermal analgesic system disclosed in U.S. Pat. Nos. 8,440,220 B2 and 8,747,889 B2, discussed above, are examples of reservoir style transdermal patches. In those reservoir transdermal patches the analgesic and antagonist layers are contained in distinct reservoir layers separated by an impermeable barrier layer and the antagonist is to release only is situations of misuse or abuse.

In another embodiment, the invention relates to an improvement in transdermal patches used to administer fentanyl or an analog thereof or another mu opioid agonist. The invention combines in a transdermal patch an effective amount of a crystalline naloxone salt, a crystalline naltrexone salt of the invention or a mixture of those crystalline salts as an opioid antagonist to provide a tamper-resistant or abuse-deterrent transdermal patch. Accordingly, the invention relates to an improved transdermal patch for administering fentanyl or an analog thereof, or for administering a mu opioid agonist, the improvement wherein the transdermal patch contains a crystalline naloxone and/or a naltrexone salt in an abuse limiting amount such as those amounts discussed above. The improved transdermal patch may any transdermal patch type known in the art, including but not limited to a drug-in-adhesive transdermal patch or a reservoir transdermal patch.

EXAMPLES

The following analytical methods were used to characterize the crystalline salt of naloxone or of naltrexones of the invention. In the examples, room temperature is identified as 22° C.

X-Ray Powder Diffraction (XRPD) Characterization:

XRPD analysis was carried out on a Siemens D5000, scanning the samples between 3 and 30.0° 2θ. The material was gently compressed onto a glass disc inserted into an XRPD sample holder. The sample was then loaded into a Siemens D5000 diffractometer running in reflection mode and analysed, using the experimental conditions described in Table 1.

TABLE 1

| Raw Data Origin | Siemens-binary V2 (.RAW) |
|---|---|
| Start Position [°2θ] | 3.0 |
| End Position [°2θ] | 35.0 |
| Step Size [°2θ] | 0.020 |
| Scan Step Time [s] | 1 |
| Scan Type | Continuous |
| Offset [°2θ] | 0.0 |
| Divergence Slit Type | Fixed |
| Divergence Slit Size [mm] | 2.0 |
| Specimen Length [mm] | Various |

TABLE 1-continued

| Receiving Slit Size [mm] | 0.20 |
|---|---|
| Measurement Temperature [° C.] | 20.0 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50 (nominal) |
| Generator Settings | 40 mA, 40 kV |
| Diffractometer Type | D5000 |
| Goniometer Radius [mm] | 217.50 |
| Incident Beam Monochromator | No |
| Diffracted Beam Monochromator | (Graphite) |
| Spinning | No |

Single Crystal X-Ray Diffraction (SXD) Characterization:

Diffraction data from a single was collected with Cu-Kα radiation (λ=1.54184 Å) at 120 K on an Agilent Supernova dual-source diffractometer equipped with an Oxford Cryosystems low-temperature device. Data were integrated and a multiscan correction for systematic errors applied (CRYSALISPRO). The structure was solved by charge flipping (Superflip) and refined against $F^2$ using all data (ShelxL-2014).

Thermogravimetric/Differential Thermal Analysis (TG/DTA):

Approximately, 10 mg of material was weighed into an open aluminium pan and loaded into a simultaneous thermogravimetric/differential thermal analyser (TG/DTA) and held at room temperature. The sample was then heated at a rate of 10° C./min from 25° C. to 300° C. during which time the change in sample weight was recorded along with any differential thermal events (DTA). Nitrogen was used as the purge gas, at a flow rate of 100 $cm^3$/min.

Example 1: Naloxone Saccharinate 1.1 Preparation of Naloxone Saccharinate by Evaporation at 22° C.

17.125 mg of naloxone (0.052 mmoles) were dissolved in 400 μl of ethanol. 9.125 mg of saccharin (0.050 mmoles) were dissolved in 300 μl of ethanol. The two solutions were mixed together and left to evaporate. Crystals of naloxone saccharinate were collected after the evaporation of the solvent.

1.2 XRPD Characterization of Naloxone Saccharinate

The experimental XRPD pattern of the naloxone saccharinate is shown in FIG. 1.

1.3 SXD Characterization of the Crystalline Naloxone Saccharinate

Figure 3:
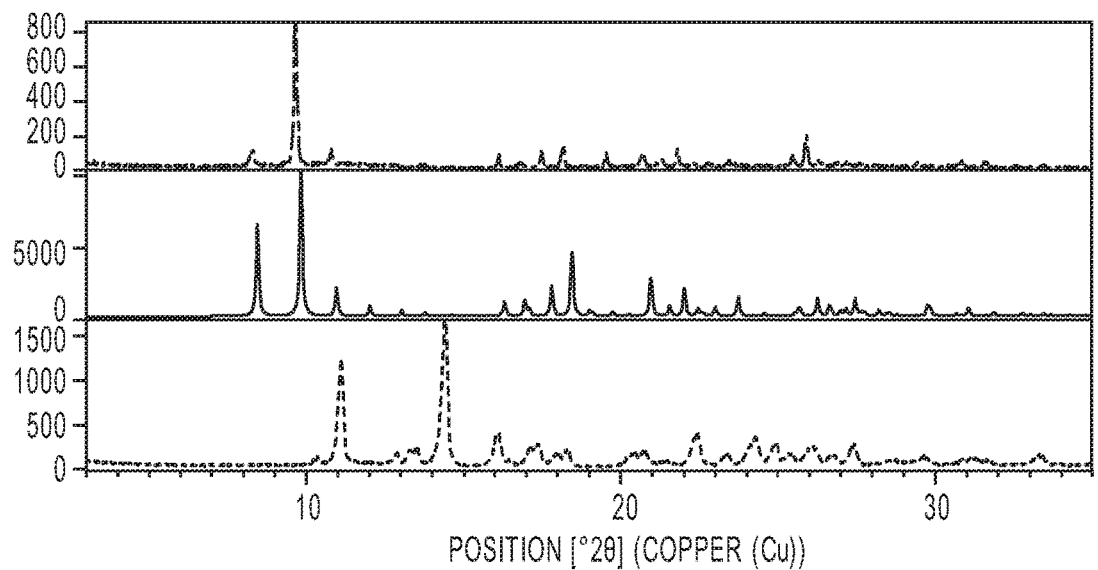
FIG. 3 is a stack of XRPD patterns of the XRPD obtained of the naloxone saccharinate prepared in Example 1.1 (red, top), the simulated powder pattern from the single crystal structure at 120K in Example 1.3 (green, middle) and naloxone (blue, bottom).

The crystal used for single crystal was prepared in Example 1.1. The single crystal data and refinement parameters for the structure measured at 120K are reported in Table 2, below. A ball and stick plot of the crystalline naloxone saccharinate at 120K showing the numbering system employed is shown in FIG. 2. The calculated XRPD pattern based on the single crystal structure of the naloxone saccharinate at 120K is shown in FIG. 3. It is to be noticed there are small temperature shifts in some of the peaks owing to the fact the experiment al powder pattern XRPD was collected at room temperature and the calculated XRPD pattern is derived from data collected at 120K. There are also small intensity differences owing to preferred orientation effects, present in the experimental pattern.

TABLE 2

Crystal structure parameters of naloxone saccharinate

| | |
|---|---|
| Molecular formula | $C_{26}H_{26}N_2O_7S$ |
| Molecular weight | 510.55 |
| Crystal system | Orthorhombic |
| Space group | $P2_12_12_1$ |
| Unit cell dimensions | a = 10.35280(3) Å |
| | b = 12.84230(5) Å |
| | c = 17.95830(5) Å |
| | α = 90° |
| | β = 90° |
| | γ = 90°. |
| Cell volume | 2387.623(13) Å$^3$ |
| Z | 4 |
| Temperature | 120(2) K |
| Radiation wave length | Cu—Kα λ = 1.54184 Å |
| Goodness of fit | 1.062 |
| R factor | 0.0231 |
| Morphology | Needle |

1.4 TG/DTA of the Naloxone Saccharinate

The thermal gravimetric analysis trace, FIG. 4, shows a loss of weight starting at around 225° C. (TGA), which is associated with an endotherm by DTA, this is due to the decomposition of the salt at high temperature.

Example 2: Naltrexone Succinates 2.1 Preparation of Methanol Solvate of Naltrexone Succinate Crystals by Methanol Evaporation at 22° C.

32.7 mg of naltrexone (0.091 mmoles) were dissolved in 200 μl of methanol. 10.76 mg of succinic acid (0.091 mmoles) were dissolved in 200 μl of methanol. The two solutions were mixed together and left to evaporate. Crystals of the methanol solvate of naltrexone succinate were collected after the evaporation of the solvent.

2.2 XRPD Characterization of Naltrexone Succinate from Methanol

The experimental XRPD pattern of the Naltrexone succinate is shown in FIG. 5.

2.3 SXD Characterization of the Naltrexone Succinate Crystal from Methanol

Figure 7:
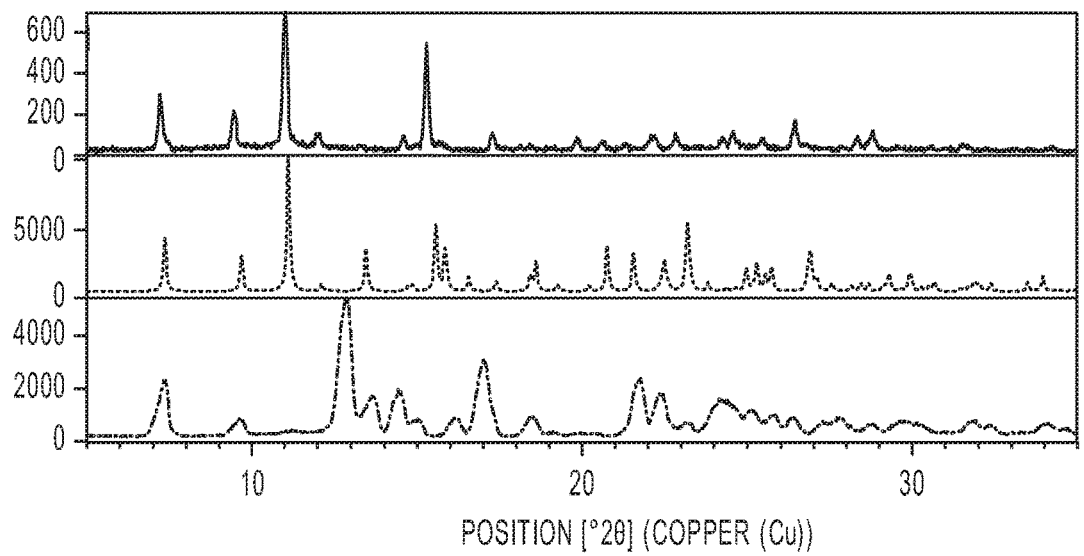
FIG. 7 is a stack of XRPD patterns of the XRPD obtained from the methanol solvate of naltrexone succinate prepared in Example 2.1 (red, top), the simulated powder pattern from the single crystal structure at 120K in Example 2.3 (green, middles) and naltrexone monohydrate (blue, bottom).

The crystal used for single crystal was prepared in Example 2.1. The single crystal data and refinement parameters for the structure measured at 120K are reported in Table 3, below. A ball and stick plot showing the molecular confirmation of protonated naltrexone in the naltrexone succinate at 120K showing the numbering system employed is shown in FIG. 6. The single crystal structure also showed the presence of one methanol per asymmetric unit (not shown in FIG. 6). The calculated XRPD pattern based on the single crystal structure of the naltrexone succinate at 120K is shown in FIG. 7. It is to be noticed there are small temperature shifts in some of the peaks owing to the fact the experiment al powder pattern XRPD was collected at room temperature and the calculated XRPD pattern is derived from data collected at 120K. There are also small intensity differences owing to preferred orientation effects, present in the experimental pattern.

TABLE 3

Crystal structure parameters of methanol solvate naltrexone succinate

| | |
|---|---|
| Molecular formula | $C_{25}H_{33}NO_9$ |
| Molecular weight | 491.52 |
| Crystal system | Orthorhombic |
| Space group | $P2_12_12_1$ |
| Unit cell dimensions | a = 7.85510(6) Å |
| | b = 15.91220(10) Å |
| | c = 18.26030(13) Å |
| | α = 90° |
| | β = 90° |
| | γ = 90°. |
| Cell volume | 2282.39(3) Å$^3$ |
| Z | 4 |
| Temperature | 120(2) K |
| Radiation wave length | Cu—Kα λ = 1.54184 Å |
| Goodness of fit | 1.045 |
| R factor | 0.0314 |
| Morphology | needle |

2.4 TG/DTA Analysis of the Naltrexone Succinate from Methanol

FIG. 8 shows the TG/DTA analysis of naltrexone succinate from methanol. The DTA curve shows a broad endotherm at around 70° C. with a corresponding weight loss of 3.1%. It is likely to be the loss of the methanol which is part of the lattice. This transition is followed by a sharp endotherm at 153.4° C. with an onset of 142.8° C. with a corresponding weight loss of 3.6%. This is followed by a small sharp endotherm at 181.8° C. These transitions are followed by an exothermic transition at 285.9° C. corresponding to the decomposition of the compound.

2.5 Preparation of Naltrexone Succinate Crystals by 1,4-Dioxane Evaporation at 22° C.

17.085 mg of naltrexone (0.048 mmoles) were dissolved in 300 μl of 1,4-dioxane. 5.90 mg of succinic acid (0.050 mmoles) were dissolved in 300 μl of 1,4-dioxane. The two solutions were mixed together and left to evaporate. Crystals of naltrexone succinate were collected after the evaporation of the solvent.

2.6 XRPD Characterization of Naltrexone Succinate from 1,4-Dioxane

The experimental XRPD pattern of the naltrexone succinate from 1,4-dioxane is shown in FIG. 9.

The invention claimed is:

1. A crystalline salt of naloxone or a crystalline salt of naltrexone selected from the group consisting of naloxone saccharinate, naltrexone succinate, and a methanol solvate of naltrexone succinate,
    wherein:
    the naloxone saccharinate is characterized by an x-ray powder diffraction (XRPD) pattern as shown in FIG. 1, a single crystal structure as shown in FIG. 2, or a thermogravimetry/differential thermal analysis (TG/DTA) trace as shown in FIG. 4;
    the methanol solvate of naltrexone succinate is characterized by an XRPD pattern as shown in FIG. 5, a single crystal structure as shown in FIG. 6 where the methanol is not shown, or a TG/DTA trace as shown in FIG. 8; and
    the naltrexone succinate is characterized by an XRPD pattern as shown in FIG. 9.

2. The crystalline salt of naloxone or the crystalline salt of naltrexone of claim 1, wherein the crystalline salt is the naloxone saccharinate.

3. The crystalline salt of naloxone or the crystalline salt of naltrexone of claim 1, wherein the crystalline salt is the naltrexone succinate.

4. The crystalline salt of naloxone or the crystalline salt of naltrexone of claim 1, wherein the crystalline salt is the methanol solvate of naltrexone succinate.

5. A drug-in-adhesive transdermal patch comprising:
a backing layer;
an adhesive layer disposed on the backing layer, the adhesive layer comprising a pressure sensitive adhesive, an opioid agonist, and the crystalline salt of naloxone or the crystalline salt of naltrexone according to claim 1 or a mixture of the crystalline salts; and
a release layer disposed on the adhesive layer opposite the backing layer.

6. A transdermal patch for administering fentanyl or an analog thereof, or for administering a mu opioid agonist, comprising the crystalline salt of naloxone or the crystalline salt of naltrexone according to claim 1 or a mixture thereof, wherein the analog is selected from the group consisting of alfentanil, lofentanil, remifentanil, sufentanil, and trefentanil.

7. The transdermal patch according to claim 6, wherein the transdermal patch is a drug-in-adhesive transdermal patch or a reservoir transdermal patch.

8. The transdermal patch according to claim 6, wherein the crystalline salt of naloxone, the crystalline salt of naltrexone, or the mixture thereof is present in terms of the molar ratio of the crystalline salt to fentanyl or an analog thereof in the range of from about 0.075:1 to about 30:1.

9. The transdermal patch according to claim 6, wherein the crystalline salt is the naloxone saccharinate.

10. The transdermal patch according to claim 6, wherein the crystalline salt is the naltrexone succinate.

11. The transdermal patch according to claim 6, wherein the crystalline salt is the methanol solvate of naltrexone succinate.

12. A drug-in-adhesive transdermal patch containing a mu opioid agonist and the crystalline salt of naloxone or the crystalline salt of naltrexone according to claim 1 or a mixture thereof, as an opioid antagonist.

13. A method of treating pain by applying a drug-in-adhesive transdermal patch according to claim 5 to the skin of a patient in need thereof.

14. The method of claim 13, wherein the pain is acute, chronic, or intermittent pain.

15. A method of treating pain by applying a transdermal patch according to claim 6 to the skin of a patient in need thereof.

16. The method of claim 15, wherein the pain is acute, chronic, or intermittent pain.

17. A method of treating pain by applying a transdermal patch according to claim 7 to the skin of a patient in need thereof.

18. The method of claim 17, wherein the pain is acute, chronic, or intermittent pain.

19. A method of treating pain by applying a drug-in-adhesive transdermal patch according to claim 12 to the skin of a patient in need thereof.

20. The method of claim 19, wherein the pain is acute, chronic, or intermittent pain.

* * * * *